United States Patent [19]

Annen et al.

[11] Patent Number: 4,619,922
[45] Date of Patent: * Oct. 28, 1986

[54] 6α, 16α-DIMETHYL CORTICOIDS

[75] Inventors: Klaus Annen, Munster-Albachten; Henry Laurent, Berlin; Helmut Hofmeister, Berlin; Michael Töpert, Berlin, all of Fed. Rep. of Germany

[73] Assignee: Schering Aktiengesellschaft, Berlin and Bergkamen, Fed. Rep. of Germany

[*] Notice: The portion of the term of this patent subsequent to Nov. 26, 2002 has been disclaimed.

[21] Appl. No.: 688,134

[22] Filed: Jan. 2, 1985

[30] Foreign Application Priority Data

Jan. 2, 1984 [DE] Fed. Rep. of Germany ....... 3400188

[51] Int. Cl.$^4$ ............................................. C07J 5/00
[52] U.S. Cl. ............................. 514/180; 260/397.45
[58] Field of Search .................................. 260/397.45

[56] References Cited

U.S. PATENT DOCUMENTS 3,054,811 9/1962 Arth et al. ..................... 260/397.45
3,312,590 4/1967 Elks et al. ..................... 260/397.45
4,555,507 11/1985 Annen et al. ............... 260/239.55 R Primary Examiner—Elbert L. Roberts
Attorney, Agent, or Firm—Millen & White

[57] ABSTRACT

6α,16α-Dimethyl corticoids of general Formula I

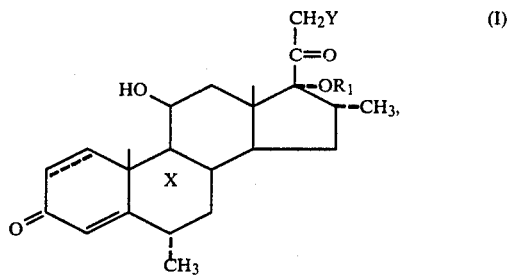

wherein
 the bond ==== is a single bond or a double bond,
 X is a hydrogen atom, a fluorine atom, a chlorine atom, or a bromine atom,
 $R_1$ is a formyl group, an alkanoyl group or alkoxyalkyl group of 2–8 carbon atoms, or a benzoyl group, and
 Y is a hydrogen atom, a chlorine atom, a hydroxy group, a formyl group, an alkanoyloxy group of 2–8 carbon atoms, or a benzoyloxy group,
are pharmacologically effective compounds.

11 Claims, No Drawings

6α,16α-DIMETHYL CORTICOIDS

BACKGROUND OF THE INVENTION

This invention relates novel 6,16-dimethyl corticoids, to pharmaceutical preparations containing them, and to compounds utilized as intermediates for their synthesis.

SUMMARY OF THE INVENTION

It is an object of this invention to provide new compounds having valuable pharmacological properties.

Upon further study of the specification and appended claims, further objects and advantages of this invention will become apparent to those skilled in the art.

In its composition aspect, the present invention is 6α,16α-dimethyl corticoids of general Formula I

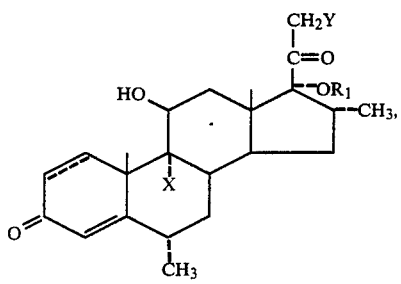

wherein
the bond ==== is a single bond or a double bond and
X is a hydrogen atom, a fluorine atom, a chlorine atom, or a bromine atom,
$R_1$ is a formyl group, an alkanoyl group or alkoxyalkyl group of 2-8 carbon atoms, or a benzoyl group, and
Y is a hydrogen atom, a chlorine atom, a hydroxy group, a formyl group, an alkanoyloxy group of 2-8 carbon atoms, or a benzyloxy group.

In another composition aspect, the present invention includes compounds of the general Formula VI

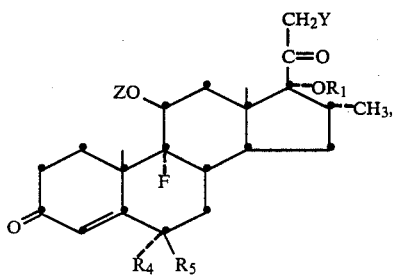

wherein $R_1$ and Y have the meanings indicated for Formula I, Z is a hydrogen atom or a trifluoroacetoxy group, and wherein $R_4$ and $R_5$ jointly represent a methylene group or two hydrogen atoms, useful in the preparation of compounds of Formula I.

The present invention also contemplates pharmaceutical compositions containing the compounds of Formula I.

DETAILED DISCUSSION

The novel 6,16-dimethyl corticoids of Formula I contain, as the substituent $R_1$, a formyl group, a linear or branched alkanoyl or alkoxyalkyl group of 2-8 (preferably 2-6) carbon atoms, or a benzoyl group. Suitable alkanoyl groups $R_1$ are, for example, the acetyl group, propionyl group, the butyryl group, the isobutyryl group, the valeryl group, the 3-methylbutyryl group, the trimethylacetyl group, or the hexanoyl groups. Especially worth mentioning as examples for alkoxyalkyl groups $R_2$ are alkoxymethyl groups, e.g. the methoxymethyl group, the ethoxymethyl group, the propoxymethyl group, the isopropoxymethyl group, the butoxymethyl group, the isobutoxymethyl group, or the tert-butoxymethyl group.

These 6,16-dimethyl corticoids contain as the substituent Y a hydrogen atom, a chlorine atom, a hydroxy group, an alkanoyloxy group of 2-8 (preferably 2-6) carbon atoms, or a benzoyloxy group. Suitable alkanoyloxy groups are, for example, those derived from the aforementioned alkanoyl groups.

The 6,16-dimethyl corticoids of general Formula I are distinguished by a pronounced anti-inflammatory activity when applied topically. Moreover, they show an excellent dissociation between desirable topical efficacy and undesirable systemic anti-inflammatory side effects.

It is to be noted that the 6,16-dimethyl corticoids of general Formula I wherein X means a hydrogen atom, a fluorine atom, or a chlorine atom are more suited for use in pharmaceutical preparations than those wherein the substituent X represents a bromine atom, since the latter preparations are less stable in galenicals but nevertheless can be so used. However, on the other hand, the 9-bromo steroids of general Formula I are valuable intermediates, using conventional methods, for the synthesis of the other 6,16-dimethyl corticoids of this invention having pharmacological efficacy.

The novel 6,16-dimethyl corticoids of general Formula I are suited, in combination with the excipients customary in galenic pharmacy, for the local treatment of contact dermatitis, eczemas of a great variety of types, neurodermatoses, erythrodermia, burns, pruritus vulvae et ani, rosacea, erythematodes cutaneous, psoriasis, lichen ruber planus et verrucosus, and similar skin disorders.

The drug specialties are prepared in the usual way by converting the active agents together with suitable additives into the desired form of application, such as, for example: solutions, lotions, ointments, creams, or plasters. In the thus-formulated medical agents, the concentration of active ingredient is dependent on the form of application. An active agent concentration of 0.001% to 1% is preferably utilized in lotions and ointments.

The novel compounds are moreover readily suitable, optionally in combination with the usual excipients and auxiliary agents, also for the preparation of inhalants that can be employed for therapy of allergic diseases of the respiratory tract, for example bronchial asthma or rhinitis.

The novel corticoids are furthermore also suitable, in the form of capsules, tablets, or dragees containing preferably 10-200 mg of active ingredient and being administered orally, or in the form of suspensions containing preferably 100-500 mg of active ingredient per dosage unit and being administered rectally, for the treatment of allergic diseases of the intestinal tract, such as colitis ulcerosa and colitis granulomatosa.

The present invention also relates to pharmaceutical preparations which contain a compound of Formula I. The pharmacologically effective compounds of this invention can be processed by conventional methods of galenic pharmacy into pharmaceutical preparations for oral or parenteral administration, e.g., to mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained released compositions can be formulated including those wherein the active compound is protected with differentially degradable coatings, e.g., by microencapsulation, multiple coatings, etc.

Suitable dosages and regimens for a given host can be determined using conventional considerations, e.g., by customary comparison of the differential activities of the subject compound and of a known agent, e.g., by means of an appropriate, conventional pharmacological protocol.

The novel 6,16-dimethyl corticoids of the invention can be produced by opening, with hydrogen fluoride, the epoxy ring of a steroid of general Formula II

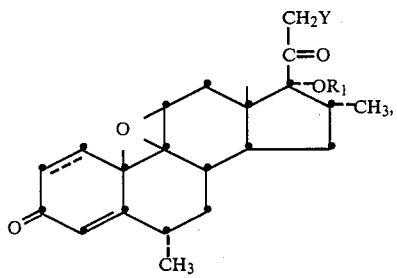

wherein ----, $R_1$ and Y have the meanings given above or chemically adding hypochlorous or hypobromous acid to the Δ9(11)-double bond of a steroid of general Formula III

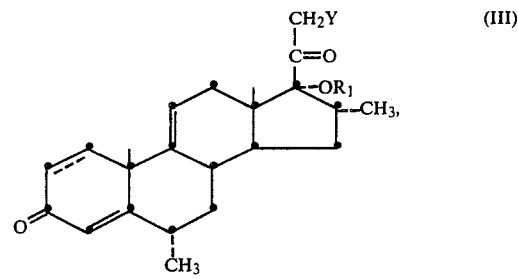

wherein ----, $R_1$ and Y have the meanings given in Formula I.

and, if desired, eliminating the 9-positioned halogen atom from the 9-bromo steroids of general Formula I. dehydrogenating a steroid of general Formula I saturated in the 1,2-position, in this position. saponifying 21-acetoxy steroids of general Formula I. or esterifying 21-hydroxy steroids of general Formula I.

In an alternate process, 6,16-dimethyl corticoids of general Formula Ia

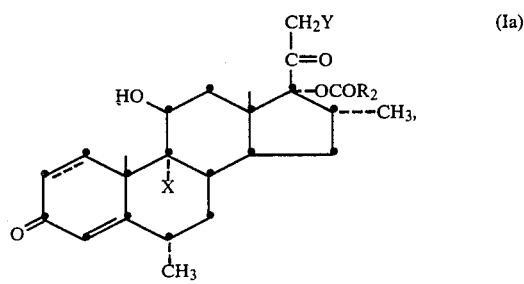

wherein
----, X and Y have the meanings given in Formula I and
$R_2$ is an alkyl group of maximally 7 carbon atoms, or a phenyl group,
are prepared by splitting the ortho ester of a steroid of general Formula IV

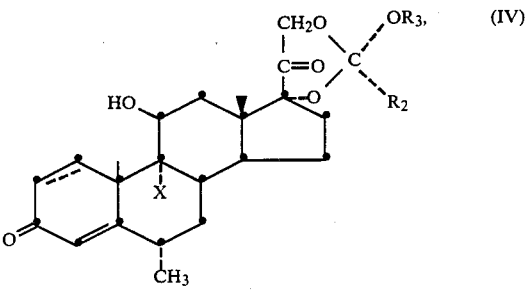

wherein
----, X and $R_2$ have the above meanings and
$R_3$ is an alkyl group of 1-4 carbon atoms,
by means of acids, trimethylsilyl chloride, or triphenylmethyl chloride, or
rearranging a 21-acyl group of a steroid of general Formula V

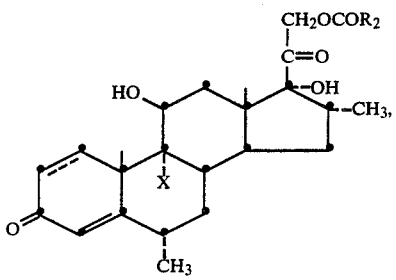

(V)

wherein ===, X and R₂ have the above-indicated meanings, and optionally esterifying a 21-positioned hydroxy group or exchanging same against hydrogen or chlorine, and optionally dehydrogenating a steroid saturated in the 1,2-position, in this position.

These processes can be carried out under the conditions as described in German Patent Applications Nos. P 26 45 105.8 and 28 03 661.5.

All of the starting materials required for the foregoing processes are known and/or readily preparable from known starting materials using fully conventional processes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius. unless otherwise indicated, all parts and percentages are by weight.

EXAMPLE 1

(a) A solution of 30 g of 21-acetoxy-9α-fluoro-17α-hydroxy-16α-methyl-11β-trifluoroacetoxy-1,4-pregnadiene-3,20-dione in 150 ml of methanol and 450 ml of tetrahydrofuran is hydrogenated with 15 g of tris(triphenyl)-phosphine rhodium(I) chloride at room temperature and under normal pressure for 20 hours. The mixture is concentrated to dryness under vacuum and the crude product is chromatographed on silica gel with a methylene chloride-acetone gradient (0–15% acetone). Yield: 24.8 g of 21-acetoxy-9α-fluoro-17α-hydroxy-16α-methyl-11β-trifluoroacetoxy-4-pregnene-3,20-dione, mp 248°–250° C.

(b) A suspension of 5 g of sodium acetate in 150 ml of chloroform and 150 ml of methylal is combined with 5 g of 21-acetoxy-9α-fluoro-17α-hydroxy-16α-methyl-11β-trifluoroacetoxy-4-pregnene-3,20-dione and, after adding 19 ml of phosphorus oxychloride dropwise, stirred for 4 hours at a bath temperature of 180° C. The reaction solution is neutralized with a saturated soda solution, the organic phase is separated and washed with water. After drying and concentrating, the crude product is purified on silica gel with a hexane-ethyl acetate gradient (0–50% ethyl acetate), thus isolating 2.9 g of 21-acetoxy-17α-hydroxy-16α-methyl-6-methylene-11β-trifluoroacetoxy-4-pregnene-3,20,-dione, mp 217°–219° C.

(c) 15 g of 21-acetoxy-17α-hydroxy-16α-methyl-6-methylene-11β-trifluoroacetoxy-4-pregnene-3,20-dione is dissolved in 225 ml of methanol and 15 ml of triethylamine. The mixture is stirred for 20 minutes at room temperature, concentrated under vacuum, and recrystallized from acetone/hexane, yielding 12.4 g of 21-acetoxy-9α-fluoro-11β,17α-dihydroxy-16α-methyl-6-methylene-4-pregnene-3,20-dione, mp 187°–189° C.

(d) Under heating, 12 g of 21-acetoxy-9α-fluoro-11β,17α-dihydroxy-16α-methyl-6-methylene-4-pregnene-3,20-dione is dissolved in 620 ml of isopropanol and, after adding 2.6 g of palladium/carbon (9.5% strength) and 36 ml of cyclohexene, agitated for 6 hours at a bath temperature of 110° C. Subsequently another 2 g of catalyst and 36 ml of cyclohexene are added, the mixture is further stirred for 20 hours, the reaction solution is suctioned off over "Celite" diatomaceous earth, thoroughly washed with methylene chloride, and concentrated to dryness under vacuum. The crude product is purified on silica gel with a hexane-ethyl acetate gradient (0–80% ethyl acetate), thus isolating 7.8 g of 21-acetoxy-9α-fluoro-11β,17α-dihydroxy-6α,16α-dimethyl-4-pregnene-3,20-dione, mp 204°–205° C.

(e) A solution of 5.2 g of 21-acetoxy-9α-fluoro-11β,17α-dihydroxy-6α,16α-dimethyl-4-pregnene-3,20-dione in 260 ml of methanol and 26 ml of water is agitated under argon with 1.3 g of potassium carbonate for 45 minutes at room temperature. After ice water precipitation, the product is worked up as usual, thus isolating 4.5 g of 9α-fluoro-11β,17α,21-trihydroxy-6α,16α-dimethyl-4-pregnene-3,20-dione, mp 242°–232° C.

(f) At a bath temperature of 130° C., about 24 ml of solvent is distilled off from the turbid mixture of 800 mg of 9α-fluoro-11β,17α,21-trihydroxy-6α,16α-dimethyl-4-pregnene-3,20-dione and 80 mg of pyridinium tosylate in 7 ml of dimethylformamide and 60 ml of hexane (cyclohexane). After a brief cooling-off period, 2 ml of triethyl orthoacetate is introduced into the warm solution and the remaining hexane (cyclohexane) is removed by distillation. Finally, the solution is combined with 0.8 ml of pyridine and concentrated under vacuum at 60° C., thus obtaining 17α,21-(1-ethoxyethylidene)-9α-fluoro-11β-hydroxy-6α,16α-dimethyl-4-pregnene-3,20-dione as an oil.

(g) A suspension of the crude 17α,21-(1-ethoxyethylidene)-9α-fluoro-11β-hydroxy-6α,16α-dimethyl-4-pregnene-3,20-dione in 24 ml of methanol is refluxed at 100° C. for one hour with a mixture of 0.96 ml of 0.1-molar aqueous sodium acetate solution and 8.5 ml of 0.1N aqueous acetic acid. The mixture is concentrated until turbid, poured on water, and extracted with ethyl acetate. The organic phase is washed with water, dried over sodium sulfate, and evaporated to dryness under vacuum. The crude product is purified on 65 g of silica gel with a hexane-acetone gradient (0–50% acetone).

Yield: 798 mg of 17α-acetoxy-9α-fluoro-11β,21-dihydroxy-6α,16α-dimethyl-4-pregnene-3,20-dione, mp 210°–211° C.

EXAMPLE 2

A solution of 650 mg of 17α-acetoxy-9α-fluoro-11β,21-dihydroxy-6α,16α-dimethyl-4-pregnene-3,20-dione in 6.5 ml of pyridine and 3.2 ml of acetic anhydride is stirred for 2 hours at room temperature and poured on an ice water-sodium chloride solution. The mixture is filtered off and worked up as usual. After crystallization from hexane/ethyl acetate, 430 mg of 17α,21-diacetoxy-9α-monofluoro-11β-hydroxy-6α,16α-dimethyl-4-pregnene-3,20-dione is isolated, mp 194°–195° C.

EXAMPLE 3

(a) Analogously to Example 1(f), 500 mg of 9α-fluoro-11β-17α,21-trihydroxy-6α,16α-dimethyl-4-pregnene-3,20-dione is reacted with 1.2 ml of triethyl orthopropionate to 17α,21-(1-ethoxypropylidenedioxy)-9α-fluoro-11β-hydroxy-6α,16α-dimethyl-4-pregnene-3,20-dione.

(b) The crude 17α,21-(1-ethoxypropylidenedioxy)-9α-fluoro-11β-hydroxy-6α,16α-dimethyl-4-pregnene-3,20-dione is hydrolyzed under the conditions of Example 1(g), worked up, and purified, thus isolating 439 mg of 9α-fluoro-11β,21-dihydroxy-6α,16α-dimethyl-17α-propionyloxy-4-pregnene-3,20-dione, mp 195°–196° C.

EXAMPLE 4

Analogously to Example 2, 400 mg of 9α-fluoro-11β,21-dihydroxy-6α,16α-dimethyl-17α-propionyloxy-4-pregnene-3,20-dione is reacted with acetic anhydride to 312 mg of 21-acetoxy-9α-fluoro-11β-hydroxy-6α,16α-dimethyl-17α-propionyloxy-4-pregnene-3,20-dione, mp 196°–198° C.

EXAMPLE 5

A solution of 500 mg of 17α,21-(1-ethoxypropylidenedioxy)-9α-fluoro-11β-hydroxy-6α,16α-dimethyl-4-pregnene-3,20-dione in 25 ml of dimethylformamide is stirred, after dropwise addition of 1 ml of trimethylchlorosilane, for 23 hours at a bath temperature of 80° C. After ice water precipitation and the usual working-up process, the crude product is purified on silica gel with a hexane-acetone gradient (0–30% acetone). Yield: 246 mg of 21-chloro-9α-fluoro-11β-hydroxy-6α,16α-dimethyl-17α-propionyloxy-4-pregnene-3,20-dione, mp 258°–260° C.

EXAMPLE 6

(a) Under the conditions of Example 1(f), 1.0 g of 11β,17α,21-trihydroxy-6α,16α-dimethyl-4-pregnene-3,20-dione is reacted with the ethyl ester of orthopropionic acid to 17α,21-(1-ethoxypropylidenedioxy)-11β-hydroxy-6α,16α-dimethyl-4-pregnene-3,20-dione.

(b) The crude 17α,21-(1-ethoxypropylidenedioxy)-11β-hydroxy-6α,16α-dimethyl-4-pregnene-3,20-dione is hydrolyzed analogously to Example 1(g), worked up, and purified, thus isolation 782 mg of 11β,21-dihydroxy-6α,16α-dimethyl-17α-propionyloxy-4-pregnene-3,20-dione.

(c) As described in Example 2, 500 mg of 11β,21-dihydroxy-6α,16α-dimethyl-17α-propionyloxy-4-pregnene-3,20-dione is reacted with acetic anhydride, worked up, and purified, thus obtaining 396 mg of 21-acetoxy-11β-hydroxy-6α,16α-dimethyl-17α-propionyloxy-4-pregnene-3,20-dione, mp 168°–170° C.

EXAMPLE 7

A solution of 2.0 g of 21-acetoxy-11β-hydroxy-6α,16α-dimethyl-17α-propionyloxy-4-pregnene-3,20-dione in 100 ml of dioxane is refluxed with 2.0 g of dichlorodicyanobenzoquinone for 24 hours. After cooling, the solid matter is suctioned off, washed with hexane, and the filtrate concentrated under vacuum. The crude product is purified on silica gel with a hexane-acetone gradient (0–40% acetone), thus isolating 1.05 g of 21-acetoxy-11β-hydroxy-6α,16α-dimethyl-17α-propionyloxy-1,4-pregnadiene-3,20-dione, mp 182°–184° C.

EXAMPLE 8

(a) A suspension prepared from 2.5 g of 9α-fluoro-11β,17α,21-trihydroxy-6α,16α-dimethyl-4-pregnene-3,20-dione and 250 mg of pyridinium toluenesulfonate in 100 ml of methyl tert-butyl ether ("Driveron" S) under argon. At an internal temperature of 58° C., 25 ml of "Driveron" S is distilled off, the mixture is cooled to 40° C., combined with 6 ml of the triethyl ester of orthobutyric acid, and subsequently refluxed for 2.5 hours so that no undissolved components are present. To this mixture is added 3 ml of pyridine and the solution is concentrated to form 17α,21-(1-ethoxybutylidenedioxy)-9α-fluoro-11β-hydroxy-6α,16α-dimethyl-4-pregnene-3,20-dione as an oil.

(b) The crude 17α,21-(1-ethoxybutylidenedioxy)-9α-fluoro-11β-hydroxy-6α,16α-dimethyl-4-pregnene-3,20-dione is hydrolyzed under the conditions of Example 1(g) to form 2.6 g of 17α-butyryloxy-9α-fluoro-11β,21-dihydroxy-6α,16α-dimethyl-4-pregnene-3,20-dione, worked up, and purified, mp 166°–167° C.

EXAMPLE 9

As described in Example 2, 2.4 g of 17α-butyryloxy-9α-fluoro-11β,21-dihydroxy-6α,16α-dimethyl-4-pregnene-3,20-dione in pyridine is reacted with 12 ml of acetic anhydride, worked up, and purified. Yield: 2.6 g of 21-acetoxy-17α-butyryloxy-9α-fluoro-11β-hydroxy-6α,16α-dimethyl-4-pregnene-3,20-dione, mp 181°–182° C.

EXAMPLE 10

Analogously to Example 7, 2.0 g of 21-acetoxy-17α-butyryloxy-9α-fluoro-11β-hydroxy-6α,16α-dimethyl-4-pregnene-3,20-dione is dehydrated with 2.0 g of dichlorodicyanobenzoquinone, worked up, and purified, thus isolating 940 mg of 21-acetoxy-17α-butyryloxy-9α-fluoro-11β-hydroxy-6α,16α-dimethyl-1,4-pregnadiene-3,20-dione, mp 229°–230° C.

EXAMPLE 11

(a) Under the conditions of Example 1(a), 1.4 g of 9α-fluoro-11β,17α,21-trihydroxy-6α,16α-dimethyl-4pregnene-3,20-dione is reacted with 3.4 ml of the triethyl ester of orthobenzoic acid to 17α,21-(1-ethoxybenzylidenedioxy)-9α-fluoro-11β-hydroxy-6α,16α-dimethyl-4-pregnene-3,20-dione as an oil.

(b) The crude 17α,21-(1-ethoxybenzylidenedioxy)-9α-fluoro-11β-hydroxy-6α,16α-dimethyl-4-pregnene-3,20-dione is hydrolyzed under the conditions of Example 1(g), worked up, and purified, thus isolating 140 mg of 17α-benzoyloxy-9α-fluoro-11β,21-dihydroxy-6α,16α-dimethyl-4-pregnene-3,20-dione as a foam.

EXAMPLE 12

(a) At 0° C., 1 ml of methanesulfonic acid chloride is added dropwise to a solution of 2:0 g of 17α-butyryloxy-9α-fluoro-11β,21-dihydroxy-6α,16α-dimethyl-4-pregnene-3,20-dione in 5 ml of pyridine. The mixture is further stirred for one hour at 0° C., poured on an ice water-sodium chloride solution, and worked up as usual, thus isolating 1.9 g of 17α-butyryloxy-9α-fluoro-11β-hydroxy-21-mesyloxy-6α,16α-dimethyl-4-pregnene-3,20-dione.

(b) A suspension of 1.9 g of 17α-butyryloxy-9α-fluoro-11β-hydroxy-21-mesyloxy-6α,16α-dimethyl-4-pregnene-3,20-dione and 1.9 g of lithium bromide in 40 ml of N-methylpyrrolidone is stirred for one hour at a bath temperature of 80° C. and worked up as usual. After chromatography on silica gel with a hexane-acetone gradient (0-30% acetone), 1.2 g of 21-bromo-17α-butyryloxy-9α-fluoro-11β-hydroxy-6α,16α-dimethyl-4-pregnene-3,20-dione is isolated.

(c) 1.2 g of 21-bromo-17α-butyryloxy-9α-fluoro-11β-hydroxy-6α,16α-dimethyl-4-pregnene-3,20-dione in 30 ml of tetrahydrofuran is sitrred under argon with 7.5 ml of tributyltin hydride as well as a spatula tip of α,α'-azobisisobutyronitrile for 6 hours at 50° C. bath temperature. The mixture is then concentrated under vacuum and the residue chromatographed with a hexane-acetone gradient (0-25% acetone), thus isolating 920 mg of 17α-butyryloxy-9α-fluoro-11β-hydroxy-6α,16α-dimethyl-4-pregnene-3,20-dione.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6α,16α-Dimethyl corticoid of the formula

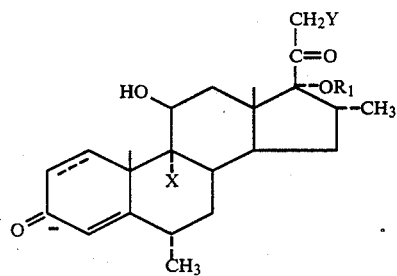

wherein
the bond ==== is a single bond or a double bond and
X is a hydrogen atom, a fluorine atom, a chlorine atom, or a bromine atom,
R₁ is a formyl group, an alkanoyl group or alkoxyalkyl group of 2-8 carbon atoms, or a benzoyl group, and
Y is a chlorine atom.

2. 21-Chloro-9α-fluoro-11β-hydroxy-6α,16α-dimethyl-17α-propionyloxy-4-pregnene-3,20-dione, a compound according to claim 1.

3. A compound of the formula

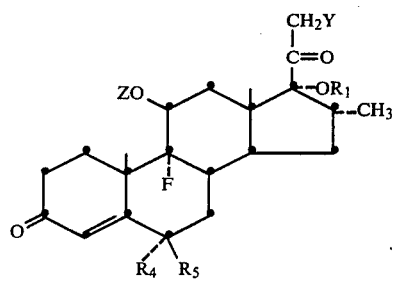

wherein
R₁ is a formyl group, an alkanoyl group or alkoxyalkyl group of 2-8 carbon atoms, or a benzoyl group, and
Y is a hydrogen atom, a chlorine atom, a hydroxy group, a formyl group, an alkanoyloxy group of 2-8 carbon atoms, or a benzoyloxy group
Z is a hydrogen atom or a trifluoroacetoxy group, and wherein R₄ and R₅ jointly represent a methylene group or two hydrogen atoms.

4. 21-Acetoxy-9α-fluoro-17-hydroxy-16α-methyl-11β-trifluoroacetoxy-4-pregnene-3,20-dione, a compound according to claim 3.

5. 21-Acetoxy-9α-fluoro-17-hydroxy-16α-methyl-6-methylene-11β-trifluoroacetoxy-4-pregnene-3,20-dione, a compound according to claim 3.

6. 21-Acetoxy-9α-fluoro-11β,17-dihydroxy-16α-methyl-6-methylene-4-pregnene-3,20-dione, a compound according to claim 3.

7. A pharmaceutical composition containing an effective antiinflammatory amount of one or two corticoids according to claim 1, and a pharmaceutically acceptable carrier.

8. A pharmaceutical composition according to claim 7, adapted for topical administration.

9. A pharmaceutical composition according to claim 8 containing 0.001-1% by weight of corticoid.

10. A method for alleviating inflammation which comprises topically administering an anti-inflammatory effective amount of a compound according to claim 1 in a pharmaceutically acceptable carrier.

11. A 6α,16α-Dimethyl corticoid of the formula

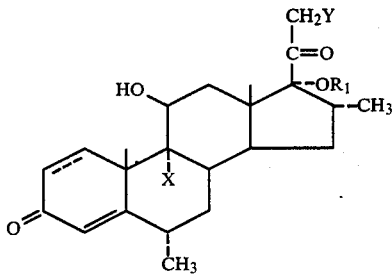

wherein
the bond ==== is a single bond or a double bond and
X is a hydrogen atom, a fluorine atom, a chlorine atom, or a bromine atom,
R₁ is alkoxyalkyl of 2-8 carbon atoms, and
Y is a hydrogen atom, a chlorine atom, a hydroxy group, a formyl group, an alkanoyloxy group of 2-8 carbon atoms, or a benzoyloxy group.

* * * * *